United States Patent [19]

Griffiths et al.

[11] Patent Number: 5,696,272

[45] Date of Patent: Dec. 9, 1997

[54] PROCESS FOR THE PRODUCTION OF 2-SUBSTITUTED 5-CHLOROIMIDAZOLE-4-CARBALDEHYDES

[75] Inventors: Gareth J. Griffiths, Visp; Gerhard C. Stucky, Brig-Glis, both of Switzerland

[73] Assignee: Lonza Ltd., Gampel/Valais, Switzerland

[21] Appl. No.: 779,364

[22] Filed: Jan. 6, 1997

[30] Foreign Application Priority Data

Jan. 5, 1996 [CH] Switzerland .................... 0025/96

[51] Int. Cl.⁶ ................................... C07D 233/68
[52] U.S. Cl. .................................... 548/333.5
[58] Field of Search ........................... 548/333.5

[56] References Cited

U.S. PATENT DOCUMENTS

| | | |
|---|---|---|
| 4,355,040 | 10/1982 | Furukawa et al. . |
| 5,442,075 | 8/1995 | Griffiths et al. . |
| 5,442,076 | 8/1995 | Gosteli et al. . |
| 5,484,939 | 1/1996 | Griffiths et al. . |
| 5,486,617 | 1/1996 | Griffiths et al. . |
| 5,508,425 | 4/1996 | Griffiths et al. . |
| 5,536,841 | 7/1996 | Griffiths et al. . |
| 5,606,072 | 2/1997 | Griffiths et al. . |

FOREIGN PATENT DOCUMENTS

| | | |
|---|---|---|
| 0579212 | 1/1994 | European Pat. Off. . |
| 0614891 | 9/1994 | European Pat. Off. . |
| 0614892 | 9/1994 | European Pat. Off. . |
| 0653422 | 5/1995 | European Pat. Off. . |
| 2804435 | 8/1978 | Germany . |

OTHER PUBLICATIONS

*Bulletin de la Societe chimique de France,* No. 3, (1971), R. Jacquier et al., pp. 1040 to 1051.

*Primary Examiner*—Patricia L. Morris
*Attorney, Agent, or Firm*—Fisher, Christen & Sabol

[57] ABSTRACT

A process for the preparation of 2-substituted 5-chloroimidazole-4-carbaldehydes of the general formula:

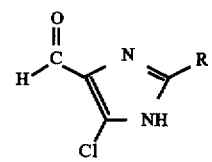

in which glycine is reacted with an imido ester of the general formula:

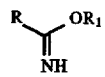

and the resultant intermediate is converted into the product by a Vilsmeier reagent. The 2-substituted 5-chloroimidazole-4-carbaldehydes are valuable intermediates for the preparation of pharmaceuticals or herbicidally active compounds.

12 Claims, No Drawings

PROCESS FOR THE PRODUCTION OF 2-SUBSTITUTED 5-CHLOROIMIDAZOLE-4-CARBALDEHYDES

BACKGROUND OF THE INVENTION

1. Field of the Invention

The invention relates to a process for the preparation of 2-substituted 5-chloroimidazole-4-carbaldehydes of the general formula:

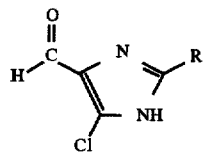

I in which R denotes hydrogen, an alkyl group, an alkenyl group, a cycloalkyl group, an arylalkyl group or an aryl group.

2. Prior Art

It is known in accordance with European Published Patent Application No. A 0,614,892 to cyclize a glycine ester hydrohalide with an imido ester to give a 3,5-dihydroimidazole and then to convert it to the target product using phosphorus oxychloride in the presence of N,N-dimethylformamide. This process has the disadvantage that the glycine methyl ester must be liberated in each case in situ from the corresponding halide. Furthermore, the glycine ester hydrohalide is a relatively expensive starting material.

The main object of the invention is to provide an economic process which takes the above-noted prior art disadvantages into account and which is able to comply with the requirements of an industrial process on a large scale. Other objects and advantages of the invention are set out herein or are obvious herefrom to one skilled in the art.

The objects and advantages of the invention are achieved by the process of the invention.

The invention involves a process for the preparation of 2-substituted 5-chloroimidazole-4-carbaldehydes of the general formula:

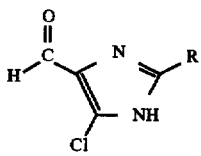

I in which R denotes hydrogen, an alkyl group, an alkenyl group, a cycloalkyl group, an arylalkyl group or an aryl group. In the first stage of the process, glycine is reacted with an imido ester of the general formula:

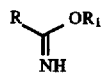

II in which R has the meaning mentioned and $R_1$ denotes an alkyl group, to give a compound of the general formula:

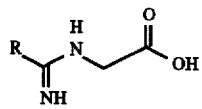

III in which R has the meaning mentioned. In the second stage, this compound is converted to the end product by a Vilsmeier reagent, which is composed of a chlorinating agent and a formamide of the general formula:

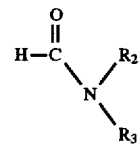

IV in which $R_2$ and $R_3$ are identical or different and denote a $(C_1-C_4)$-alkyl group or an aryl group.

Preferably the compound of the general formula III is not isolated before the second stage. Preferably the reaction in the first stage is carried out at a pH between 4 and 12 and at a temperature between −20° C. and 80° C. Preferably the chlorinating agent used in the Vilsmeier reagent is phosphorus oxychloride. Preferably the formamide of the general formula IV used in the Vilsmeier reagent is N,N-dimethylformamide. Preferably the molar ratio of chlorinating agent to formamide of the general formula IV in the Vilsmeier reagent is between 1 to 1 and 4 to 1. Preferably the reaction with the Vilsmeier reagent proceeds at a temperature between 60° C. and 200° C.

The 2-substituted 5-chloroimidazole-4-carbaldehydes of the general formula I are important intermediates for the preparation of hypotensive pharmaceuticals (U.S. Pat. No. 4,355,040) or herbicidally active compounds (German Patent No. A 2,804,435).

DETAILED DESCRIPTION OF THE INVENTION

In formulae, I, II, III and IV, the general substituents R, $R_1$, $R_2$ and $R_3$ have the following meanings:

An alkyl group is taken to mean a straight-chain or branched $(C_1-C_6)$-alkyl group, in particular methyl, ethyl, n-propyl, isopropyl, n-butyl, isobutyl, t-butyl, pentyl and its isomers, or hexyl and its isomers. A preferred alkyl group for R is the n-butyl group. A preferred alkyl group for $R_1$ is a $(C_1-C_4)$-alkyl group, particularly preferably methyl.

An alkenyl group is taken to mean a straight-chain or branched $(C_1-C_6)$-alkenyl group, in particular 1-propenyl, 2-propenyl, 1-butenyl, 2-butenyl, 3-butenyl, pentenyl and its isomers, or hexenyl and its isomers. A preferred alkenyl group is 2-butenyl or 3-butenyl.

Cycloalkyl is expediently taken to mean cyclopropyl, cyclobutyl, cyclopentyl or cyclohexyl.

An arylalkyl group expediently has the meaning phenyl-$(C_1-C_6)$-alkyl, preferably benzyl. Aryl correspondingly has the preferred meaning of phenyl.

The aryl group can have one or more substituents, such as, alkyl, halo, nitro or amino, on its aromatic nucleus.

The term halogen expediently includes chlorine, bromine or iodine, preferably chlorine.

In the first step of the process according to the invention, glycine is reacted with an imido ester of the general formula:

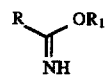

II in which R has the meaning mentioned above and $R_1$ denotes an alkyl group, to give a compound of the general formula:

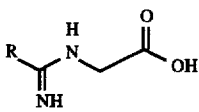

III in which R has the meaning mentioned above.

Expediently, the reaction is performed in the first stage at a pH between 4 and 12, preferably at 5 to 9, and at a temperature generally between −20° C. and 80° C., preferably between 0° C. and 30° C.

The glycine is customarily present suspended in a suitable solvent, such as an aliphatic alcohol such as methanol or ethanol, optionally mixed with water. The imido ester can be added in the form of a solution in an inert solvent, such as toluene, chlorobenzene, or an aliphatic alcohol. The reaction partners in the first stage are expediently used stoichiometrically.

After a reaction time expediently of 2 hours to 48 hours, the resulting compound of the general formula III can be isolated from the reaction mixture in a manner known to those skilled in the art, but preferably it is not isolated and instead is further reacted directly to give the end product.

In the second and last stage, the compound of the general formula III is converted into the end product by so-called Vilsmeier reagent.

The Vilsmeier reagent is expediently composed of a chlorinating agent and a formamide of the general formula:

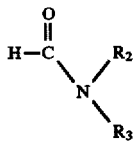

IV in which $R_2$ and $R_3$ are identical or different and denote a $(C_1-C_4)$-alkyl group or an aryl group. A preferred formamide is N,N-dimethylformamide.

The chlorinating agent used expediently is phosphorus oxychloride, thionyl chloride, phosgene or phosgene-releasing compounds, phosphorus trichloride or phosphorus pentachloride. A preferred chlorinating agent is phosphorus oxychloride.

Expediently the molar ratio of chlorinating agent to formamide of the general formula IV in the Vilsmeier reagent is between 1 to 1 and 4 to 1. The Vilsmeier reagent is expediently used in excess, serving at the same time as a solvent. However, it is also possible to add an inert solvent such as toluene, chlorobenzene or xylene.

The reaction temperature for the reaction in the second stage expediently is between 60° C. and 200° C.

In the course of this reaction, an N,N-substituted aminomethyleneimidazole of the general formula:

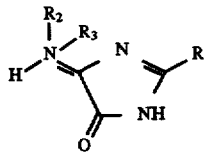

V in which R, $R_2$ and $R_3$ have the meaning mentioned, is formed as an intermediate.

This intermediate is the subject-matter of the European Published Patent Application No. A 0,653,422.

After a reaction time of generally 1 hour to 24 hours, the corresponding 2-substituted 5-chloroimidazole-4-carbaldehyde can be obtained in good yield and purity in a manner known to those skilled in the art, expediently by treating the reaction mixture with water and extraction with a suitable solvent.

EXAMPLE 1

Preparation of (Pentanimidoylamino)acetic Acid

A stirred suspension of glycine (18.77 g, 0.25 mol) in methanol (80 ml) and water (4.5 ml) was cooled to 0° C. and adjusted to pH 9.6 by adding 30 percent strength sodium hydroxide solution. Methyl pentanimidate (68.81 g of a 42 percent strength solution in toluene=0.25 mol) was added to this suspension over the course of 5 minutes. After stirring for 18 hours at room temperature, the suspension was filtered, and the filter cake was washed with toluene (75 ml) and dried. The yield of the title compound was 25.45 g (purity>95 percent by H-NMR), 64 percent based on glycine. Other data concerning the title compound was:

$^1$H-NMR (CH$_3$OD, 400 MHz) δ 0.94 (3H, t); 1.43 (2H, m); 1.70 (2H, m); 2.50 (2H, t); 3.75 (2H, s).

EXAMPLE 2

Preparation of (Pentanimidoylamino)acetic Acid

A stirred suspension of glycine (18.77 g, 0.25 mol) in methanol (80 ml) and water (4.5 ml) was cooled to 0° C. and adjusted to pH 9.6 by adding 30 percent strength sodium hydroxide solution. Methyl pentanimidate (67.12 g of a 42.9 percent strength solution in toluene=0.25 mol) was added to this suspension over the course of 7 minutes. The reaction mixture was stirred for 5 hours at room temperature. Methanol and water were then distilled off at a reduced pressure of 30 mbar to 150 mbar. In total, 250 ml of toluene was added during this distillation. The mixture was then filtered, and the filter cake washed with toluene (75 ml) and dried. The yield of the title compound was 39.61 g (purity approximately 90 percent by H-NMR), 90 percent based on glycine.

EXAMPLE 3

Preparation of 2-Butyl-5-chloroimidazole-4-carbaldehyde

Phosphorus oxychloride (43.80 g, mmol) was added to a suspension of (pentanimidoylamino)acetic acid (15.82 g, 100 mmol) in toluene (75 ml) in the course of 5 minutes. The mixture was heated to 80° C. and then admixed with N,N-dimethylformamide (20.57 g, 280 mmol) in the course of 7 minutes. The temperature rose in the course of this to 96° C. After stirring for 2 hours at 100° C., the mixture was cooled to 30° C. The reaction mixture was then poured with stirring into 80 ml of water in such a manner that the temperature could always be kept below 30° C. After addition of ethyl acetate (80 ml) and Celite (5 g), the pH of the mixture was adjusted to 1.2 with 30 percent strength sodium hydroxide solution. The mixture was filtered, then phase separation took place at 30° C. The organic phase was washed twice with water and then concentrated to dryness. The title product was obtained in a yield of 13.39 g (HPLC purity 81.4 percent), 50 percent based on (pentanimidoylamino)acetic acid.

EXAMPLE 4

Preparation of 2-Butyl-5-chloroimidazole-4-carbaldehyde [Without Isolation of (Pentanimidoylamino)acetic Acid]

A white suspension of 37.91 g (0.50 mol) of glycine, 9.0 g (0.50 mol) of water and 160 ml of methanol was cooled to 0° C. The pH was adjusted to 9.5 by addition of 30 percent strength sodium hydroxide solution. 140.46 g of a solution of methyl pentanimidate (41 percent strength=0.50 mol) in toluene was added dropwise in the course of 11 minutes, so that the temperature could be kept at 0° C. The reaction mixture was stirred for 20 hours at room temperature, after which the pH was adjusted from 10.13 to 7.0 by the addition of concentrated sulfuric acid. 500 ml of toluene was added and methanol and water were distilled off under vacuum. After the distillation, 72.6 g of toluene was added. The weakly yellowish suspension was cooled to 0° C. and 219.0 g (1.40 mol) of phosphorus oxychloride was added in the course of 11 minutes. After 20 minutes, the mixture was heated to 80° C., 102.9 g (1.40 mol) of dimethylformamide was added, the mixture was heated for 2 hours at 100° C., allowed to cool to 35° C. and, with stirring, poured into 350 ml of water so that the temperature could be kept below 30° C. The mixture was admixed with 300 ml of ethyl acetate and 20 g of Celite, and stirred for 15 minutes at 25° to 30° C. The pH was adjusted to 1.20 by the addition of 2.75 ml of 30 percent strength sodium hydroxide solution. The Celite was filtered off with suction at approximately 30° C. and the phases were separated at approximately 30° C. The organic phase was washed twice with water and concentrated to dryness. The yield of the title compound was 68.1 g (HPLC purity 85.0 percent), 62 percent based on glycine.

EXAMPLE 5

Preparation of (Benzimidoylamino)acetic Acid

A white suspension of glycine (3.81 g, 50 mmol) in water (0.9 g) and methanol (16 ml) was stirred at room temperature, adjusted to pH 9.6 by the addition of sodium hydroxide solution and admixed with ethyl benzimidate (7.69 g, 50 mmol). The mixture was heated for 1 hour at 50° C. and allowed to cool at room temperature. The solid was filtered off, washed with toluene and dried at room temperature/30 mbar. The yield of the title compound was 6.81 g (approximately 95 percent pure by H-NMR), 74 percent based on glycine. Other data concerning the title compound was:

$^1$H-NMR (D$_2$O, 400 MHz) δ 4.09 (2H, s); 7.63 (2H, m); 7.76 (3H, m).

EXAMPLE 6

Preparation of 5-Chloro-2-phenyl-3H-imidazole-4-carbaldehyde

A suspension of (benzimidoylamino)acetic acid (4.38 g, 25 mmol) in toluene (25 ml) at 0° C. was admixed over the course of 5 minutes with phosphorus oxychloride (10.73 g, 70 mmol). After addition of toluene (19 ml) the mixture was heated to 80° C., admixed with N,N-dimethylformamide (5.12 g, 70 mmol) and reacted further for 2 hours at 100° C. The reaction mixture was poured into water (19 ml) so that the temperature could be kept below 30° C., and the reaction flask was rinsed with ethyl acetate (15 ml). The reaction mixture was admixed with Celite (2.25 g), stirred for 0.5 hours at 25° C., and adjusted to pH 1.2 by the addition of 30 percent strength sodium hydroxide solution (7.3 ml). The mixture was filtered and the phases were separated. The organic phase was washed twice with water and concentrated to dryness. The yield of the title compound was 4.13 g (approximately 95 percent pure by H-NMR), 76 percent based on (benzimidoylamino)acetic acid. Other data concerning the title compound was:

$^1$H-NMR (CDCl$_3$, 400 MHz) δ 7.5 (3H, m); 8.1 (2H, m); 9.77 (1H, s); 11.7 (1H, br. s).

What is claimed is:

1. A process for the preparation of a 2-substituted 5-chloroimidazole-4-carbaldehyde of the formula:

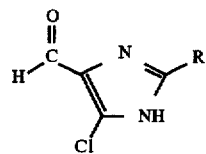

wherein R is hydrogen, alkyl, alkenyl, cycloalkyl, arylalkyl or aryl, comprising: in a first stage, reacting glycine with an imido ester of the formula:

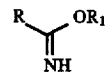

wherein R has the meaning recited above and R$_1$ is alkyl, to give a compound of the formula:

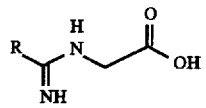

wherein R has the meaning recited above; and in a second stage, converting the compound of formula III to the 2-substituted 5-chloroimidazole-4-carbaldehyde of formula I by a Vilsmeier reagent, which is composed of a chlorinating agent and a formamide of the formula:

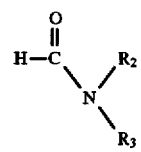

wherein R$_2$ and R$_3$ are identical or different and each is a (C$_1$–C$_4$)-alkyl or an aryl.

2. The process according to claim 1, wherein the compound of the formula III is not isolated before being converted in the second stage.

3. The process according to claim 2 wherein the reaction in the first stage is carried out at a pH between 4 and 12 and at a temperature between −20° C. and 80° C.

4. The process according to claim 3 wherein the chlorinating agent used in the Vilsmeier reagent is phosphorus oxychloride.

5. The process according to claim 4 wherein the formamide of the formula IV used in the Vilsmeier reagent is N,N-dimethylformamide.

6. The process according to claim 5 wherein the molar ratio of chlorinating agent to formamide of the formula IV in the Vilsmeier reagent is between 1 to 1 and 4 to 1.

7. The process according to claim 5 wherein the reaction with the Vilsmeier reagent proceeds at a temperature between 60° C. and 200° C.

8. The process according to claim 1 wherein the reaction is carried out in the first stage at a pH between 4 and 12 and at a temperature between −20° C. and 80° C.

9. The process according to claim 1 wherein the chlorinating agent used in the Vilsmeier reagent is phosphorus oxychloride.

10. The process according to claim 1 wherein the formulae of the formula IV used in the Vilsmeier reagent is N,N-dimethylformamide.

11. The process according to claim 10 wherein the molar ratio of chlorinating agent to formamide of the formula IV in the Vilsmeier reagent is between 1 to 1 and 4 to 1.

12. The process according to claim 10 wherein the reaction with the Vilsmeier reagent proceeds at a temperature between 60° C. and 200° C.

* * * * *